United States Patent [19]
Zwirn

[11] Patent Number: 4,827,141
[45] Date of Patent: May 2, 1989

[54] SUBRESOLUTION ELEMENT SPATIAL MEASUREMENT TECHNIQUE

[75] Inventor: Robert Zwirn, Los Angeles, Calif.

[73] Assignee: Hughes Aircraft Company, Los Angeles, Calif.

[21] Appl. No.: 113,835

[22] Filed: Oct. 26, 1987

[51] Int. Cl.$^4$ .............................................. G01B 11/04
[52] U.S. Cl. ..................................... 250/560; 250/561; 356/386
[58] Field of Search ................ 250/560, 561; 356/386, 356/387

[56] References Cited

U.S. PATENT DOCUMENTS

| | | | |
|---|---|---|---|
| 3,710,128 | 1/1973 | Kubisiak | 250/560 |
| 3,782,834 | 1/1974 | Fujimori et al. | 250/560 |
| 4,142,105 | 2/1979 | Erdmann | 250/560 |
| 4,697,088 | 9/1987 | Bishop | 250/560 |

Primary Examiner—Edward P. Westin
Attorney, Agent, or Firm—William J. Streeter; A. W. Karambelas

[57] ABSTRACT

An inspection system incorporating a subresolution element spatial measurement technique is disclosed. The system of the invention includes a scanner for scanning, with a beam of electromagnetic energy, an object area having first and second contiguous sections of first and second degrees of reflectivity or transmissivity with respect to the beam. A detector assembly is disposed to receive energy reflected from or transmitted through the object area and to provide a first signal having a first measured value S representing the amplitude of energy instantaneously reflected from or transmitted through the object area. Processing apparatus is included for analyzing the first signal and computing the ratio F of one of the first or second sections as a fraction of the total area instantaneously illuminated by the beam.

13 Claims, 3 Drawing Sheets

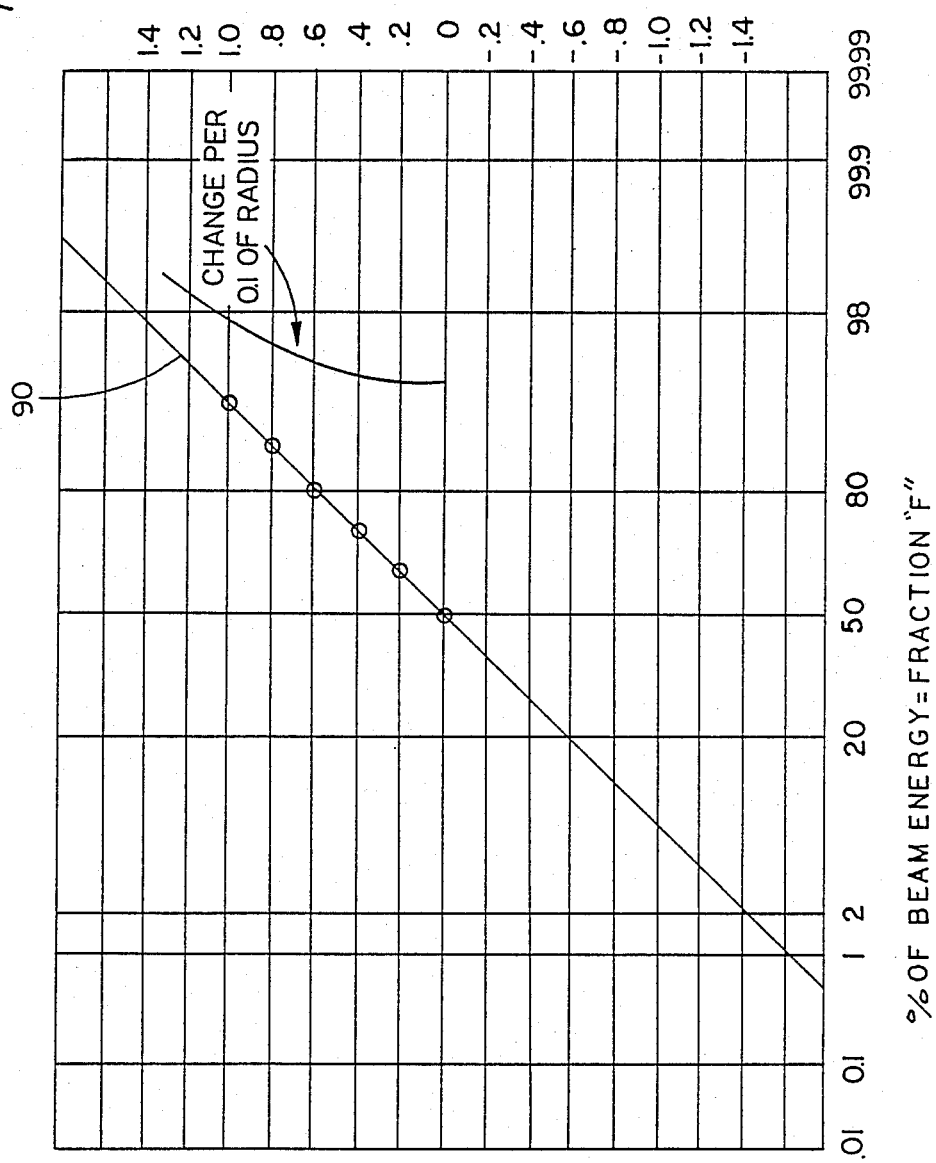

SUBRESOLUTION ELEMENT SPATIAL MEASUREMENT TECHNIQUE

BACKGROUND OF THE INVENTION

1. Field of the Invention

This invention relates to optical systems. More specifically, this invention relates to optical systems utilized in automatic inspection equipment.

While the present invention is described herein with reference to an illustrative embodiment for a particular application, it is understood that the invention is not limited thereto. Those having ordinary skill in the art and access to the teachings provided herein will recognize additional modifications, applications and embodiments within the scope of the present invention.

2. Description of the Related Art

For many applications, the speed and efficiency associated with optical, and other noncontact, measurement and inspection systems has afforded substantial reductions in manufacturing costs. In printed circuit board fabrication, for example, optical systems, such as the Opti III made by Hughes Aircraft Company, verify the dimensions between metal and substrate with heretofore acceptable resolution.

These conventional systems typically scan a spot beam across a board under test. Where the spot illuminates metal, e.g. copper, the reflected light is detected at one amplitude and where the spot illuminates the board, a second amplitude is detected. The detected signals are compared to a threshold to make the desired measurement. The tolerance of the measurement is the diameter of the spot. That is, the measurement is often inaccurate when the spot straddles both copper and board.

Accordingly, efforts to improve the performance of these systems have focused on reducing the diameter of the spot. However, this approach has been found to be problematic. One reason results from the higher costs associated with generating smaller spots. That is, smaller spots require larger, more expensive lenses and associated optical equipment.

A more significant limitation derives from the added processing requirements. To utilize a spot having a diameter 1/n times smaller than that of a conventional spot, where n is a number, necessitates an increase in the load on the processor by a factor of $n^2$. This is due to the need to process n times as many spots in the inscan direction and n times as many spots in the crossscan direction. Thus, with this approach, a doubling in resolution requires a four fold increase in processing speed and power. There are also comparable associated increases in other key components and parameters such as memory, bandwidth, power, number of detectors, and system noise.

There is therefore a need in the art for a an improved inspection system or a technique by which the performance of conventional measuring systems may be improved without forcing added burdens on tee associated optical and processing systems.

SUMMARY OF THE INVENTION

The need in the art is addressed by the improved inspection system of the present invention which incorporates a subresolution element spatial measurement technique of the present invention. The system of the invention includes means for scanning, with a beam of electromagnetic energy, an object area having first and second contiguous sections of first and second degrees of reflectivity with respect to the beam. Detecting means are disposed to receive energy reflected from the object area and to provide a first signal having a first measured value S representing the amplitude of energy instantaneously reflected from the object area. Processing means are included for analyzing the first signal and computing the ratio F of the first section to the second section as a fraction of the total dimension instantaneously illuminated by the beam.

The technique of the invention is for use in an optical system having means for scanning with a beam of electromagnetic energy, an object area having first and second contiguous sections of first and second degrees of reflectivity with respect to the beam and detecting means disposed to receive energy reflected from the object area and to provide a first signal. The subresolution element spatial measurement technique of the present invention includes the steps of measuring the amplitude of the first signal to provide a first measured value S representing the amplitude of energy instantaneously reflected from the object area and analyzing the first signal and computing the ratio F of the first section to the second section as a fraction of the total dimension instantaneously illuminated by the beam.

BRIEF DESCRIPTION OF THE DRAWINGS

FIG. 4 is a graph of a Gaussian spot energy distribution as a function of edge location.

DESCRIPTION OF THE INVENTION

Figures 1, 3:
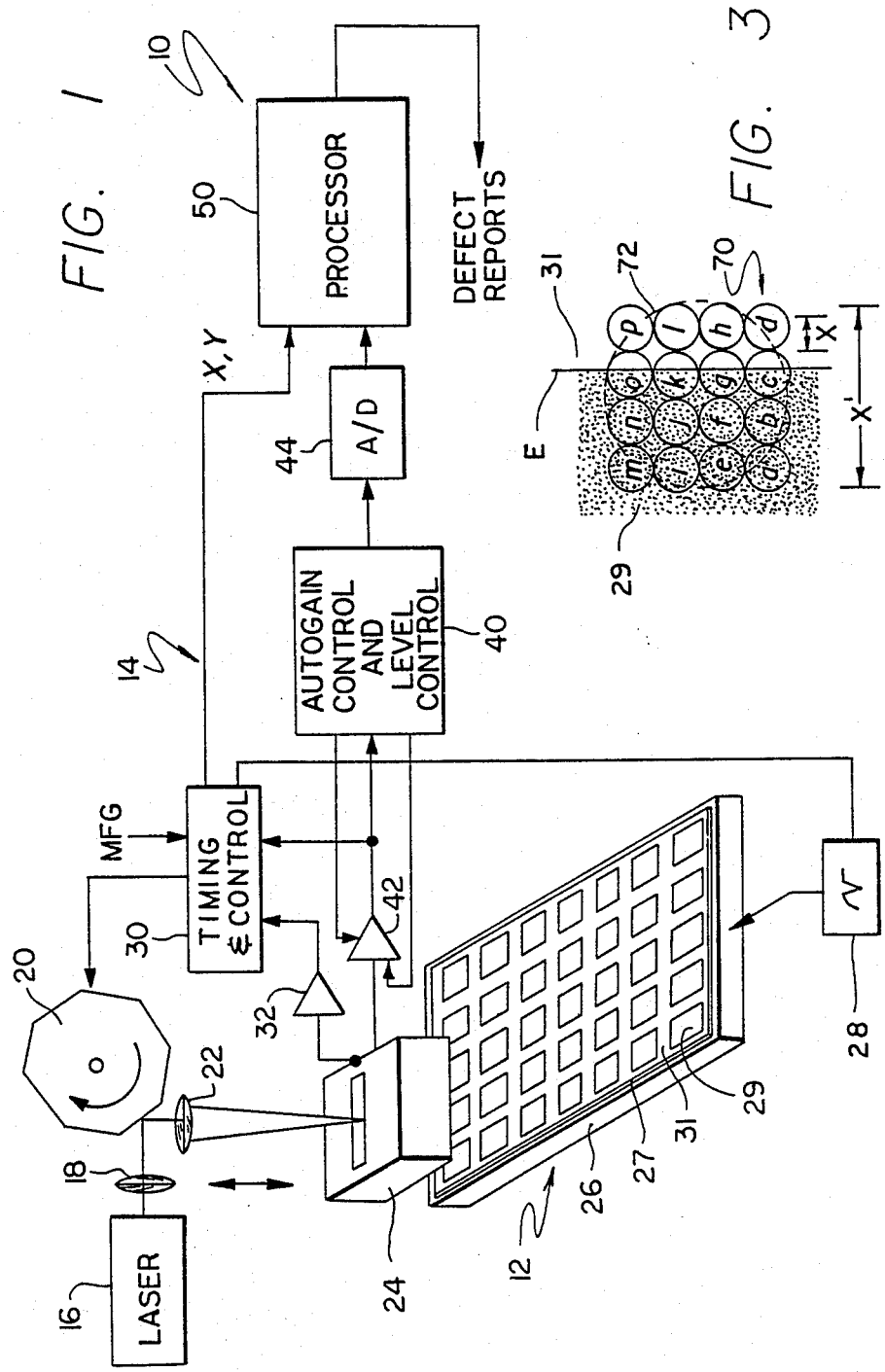
FIG. 1 is a diagrammatic representation of an illustrative embodiment of the present invention.
FIG. 3 is an illustrative scan map utilized to explain the advantageous teachings of the present invention.

FIG. 1 shows a simplified illustrative block diagram of the improved inspection system 10 of the present invention. The system 10 includes a conventional scanning subsystem 12 and a novel processing subsystem 14. The scanning subsystem 12 includes a laser 16, a first lens 18, a rotating polygon scanner 20 and a second lens 22. The laser 16 is a conventional laser chosen to to meet system specifications in a manner known to those skilled in the art. The laser 16 provides an output beam which is focused to a spot of a diameter 'd' by the first and second lenses 18 and 22. The polygon scanner 20, an off-the-shelf device, has a reflective perimeter and is positioned between the lenses 18 and 22 to reflect the beam in a predetermined scanning pattern. A typical scanning pattern is one in which the beam moves horizontally across an object area, is moved vertically down one row, and is again scanned horizontally across the object area. The horizontal scan is regarded as the inscan while the vertical scan is the cross-scan. While this scanning pattern is adopted for the purpose of explaining the advantages of the present invention, the invention is not limited thereto. The present invention is equally applicable to other fixed and variable scanning patterns as will be readily apparent to those skilled in the art.

The focused beam, now a spot beam, passes through a detector assembly 24 to scan an area (the object area) on a table 26. The detector assembly 24 includes one or more photodetectors mounted to receive light which is reflected from the object area. In the illustrative application, a printed circuit board with a typically intricate pattern of metalization, e.g. copper, is mounted within the object area on the table 26.

The table 26 is moved at velocity 'v' in a direction perpendicular to the scan by a precision positioning mechanism 28. The beam scan is governed by a timing and control circuit 30. It senses the beginning of a scan pulse from an amplifier 32 and controls the direction and rate of rotation of the polygon scanner while governing the movement of the table 26. The positioning mechanism 28 and the timing and control circuit 30 are well known in the art and need not be of any unique design for the present invention.

Figure 2A:
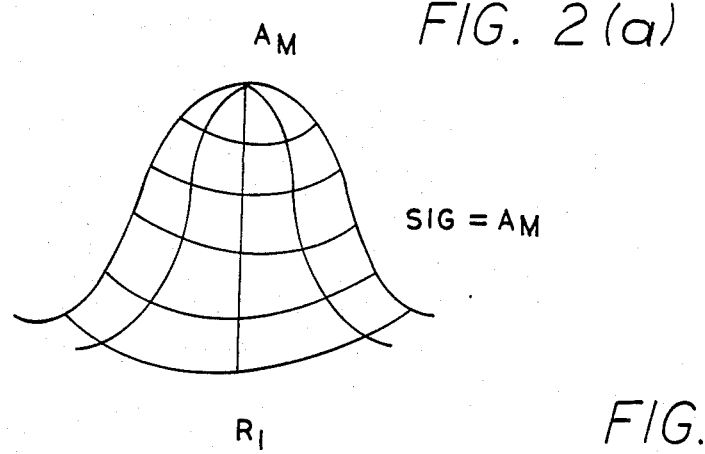
FIG. 2(a) is representative of the video return for an exclusively metal section of a printed circuit board under inspection by the system of the present invention.
Figure 2B:
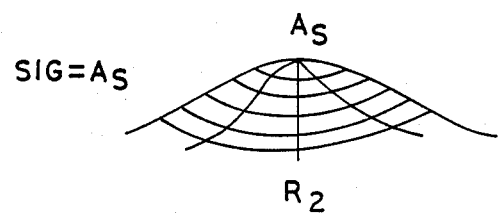
FIG. 2(b) is representative of the video return for an exclusively substrate section of a printed circuit board under inspection by the system of the present invention.

Thus, the beam is sequentially scanned across and down the board 27. When the spot illuminates an exclusively metal section in the object area having a first reflectivity R1, light is reflected and detected by the detector assembly 24. The return from the detector assembly 24, for the exclusively metal section, has an amplitude $A_M$ and is represented in FIG. 2(a). Similarly, FIG. 2(b) represents the return from the detector assembly 24 for an exclusively substrate section having a second reflectivity $R_2$. The amplitude of the return for the exclusively substrate section is $A_S$. The amplitude of the return S is generally the area under the two dimensional curve of FIG. 2(a) or 2(b) and is given by equation [1] below:

$$S = FA_M + (1-F)A_S \quad [1]$$

where F is the fraction of the total area within the spot that is metal. Typically, $A_M$ and $A_S$ are determined at calibration and stored. S is the measured return. Thus, F may be determined:

$$F = (S - A_S)/(A_M - A_S) \quad [2]$$

Figure 2C:
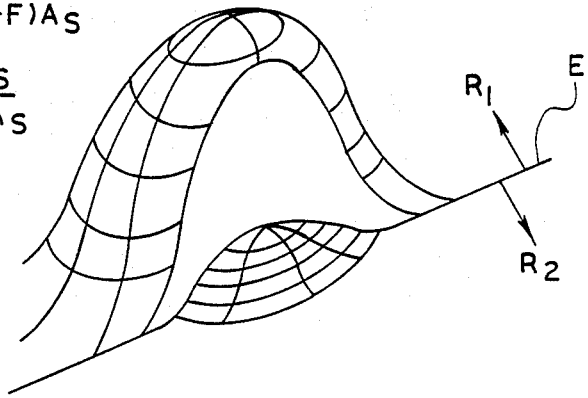
FIG. 2(c) is representative of the video return for a spot illuminating a section having both metal and substrate.

A typical return is shown in FIG. 2(c). The processing subsystem 14 analyzes the return and determines the ratio F of metal to total illuminated area. This provides an inference as to the location of the edge E between the metal and the substrate sections 29 and 31 respectively of the board 27. This information is then processed in a conventional manner to provide the exact location of the edge E. As shown in FIG. 1, the processing subsystem 14 includes an automatic gain and level control circuit 40 which receives the output of the detector assembly 24 through a conditioning amplifier 42. The gain and level controlled video output of the circuit 40 is digitized by an analog-to-digital (A/D) converter 44 and input to a processor 50. The A/D converter 44 and the processor 50 complete the processing subsystem 14.

The processor 50 receives the beam address from the timing and control circuit 30 and uses it to store the digitized returns. The processor 50 then retrieves the values of $A_M$ and $A_S$ from memory and calculates the ratio F by the relationship of equation 2 above. This provides an indication of the ratio of the metalized section to the total area instantaneously illuminated by the spot. By comparing the value stored for the returns in the vicinity of a center area, the orientation of the edge can also be determined. For example, if the prior and subsequent in-scan returns are substantially equal to the instant return, the edge may be assumed to be horizontal. Similarly, if the prior and subsequent cross-scan returns are substantially equal to that of the instant return, the edge may be assumed to be vertically oriented. With knowledge of the ratio of metal to substrate within a spot, and with knowledge of the orientation of the edge, the processor 50 may determine the location of the edge with enhanced accuracy.

The advantageous operation of the present invention is best revealed with reference to the illustrative scan map of FIG. 3. It shows a conventional array of spots 70 labeled 'a' through 'p' which illuminate the metal section 29, the substrate section 31 and the edge E therebetween. A comparable conventional system would typically have a threshold detector, in place of the A/D converter 44 of the present invention, and would utilize a binary processing scheme such that the returns from the sequentially scanned spots e, f, g, and h would be interpreted as 1, 1, 1, and 0 respectively, where a "1" would indicate the detection of metal and a "0" would indicate the detection of substrate. As the spots e, and f, illuminate all metal and the spot h illuminates all substrate, there would be no ambiguity in the detection by the conventional system. However, those spots on the edge E, i.e. c, g, k, and o, would be subject to some ambiguity. That is, these spots will be interpreted as being on the edge because the amplitudes of the associated returns would be between metal and substrate threshold levels, e.g. $A_M$ and $A_S$ respectively. The conventional systems, however, would be unable to determine the location of the edge E within the spot c, g, k, or o.

Improvements in the resolution of conventional systems has heretofore been limited to increasing the number of spots. The present invention provides increased resolution without the addition of a larger number of smaller spots. The present invention accomplishes this by examining the amplitude of the return rather than comparing it to a threshold. Using the example above and equation [2], the amplitude of the return S would equal $A_M$ for spots e and f for which the fraction F would equal 1 in accordance with equation [2]. Similarly, spot h would return an amplitude S of $A_S$ and a value for F of '0'. However, the spot g sitting with say 75% on the edge E, would return an amplitude of say 0.75. In addition, as the spots c directly above and k directly below the current scan spot g would provide the same value for F of 0.75, the edge E may be assumed to be vertically oriented. This allows for a more precise calculation of the position of the edge E within the current scan spot g.

It will be appreciated by those skilled in the art that the present invention allows the scanning spot diameter x to be increased to x' as shown in FIG. 3 for the alternative phantom spot 72. This would result in a reduction in the number of spots that must be stored and processed, and a corresponding increase in processing speed, in accordance with the ratio $(x'/x)^2$ as mentioned above, while retaining the resolution of the conventional system.

From another perspective, consider that the phantom spot 72 represents a conventional spot and the smaller spots 70 represent a proposed increased in the number of spots to provide additional resolution. From the above discussion, it is apparent that the edge E samples the spot 72 at say 75% of its value giving a fraction F of 0.75. Using adjacent spots (not shown) in the manner described above, provides an indication of the orientation of the edge E so that its location may be precisely calculated. Edge location is facilitated with a precision greater than that resulting from the proposed 16 fold increase in the number of spots using conventional techniques. Moreover, the improvement in resolution afforded by the system of the present invention, is realized with no appreciable additional burden, viz speed, memory etc., on the system processor.

The present invention has been described herein with reference to a particular embodiment for a particular application. Nonetheless, the invention is not limited thereto. Those of ordinary skill in the art and access to the teachings provided herein will recognize additional modifications, applications, and embodiments within the scope thereof. For example, the invention is not limited to use in a printed circuit board inspection systems. Precision location of any discontinuity in an otherwise locally uniform surface can be achieved. Thus, the teachings of the present invention may be used to extract precision measurements from X-ray and ultrasound equipment for example. It may be used as a photointerpretation aid as for example to provide quantitative data on specific object sizes and also dimensions between objects for future comparison or to construct identification features for mathematical I.D. calculations. Nor are the applications limited to the processing of optical spots. Other applications include magnet domains, gamma rays, the above-mentioned X-rays and etc.

Further, the invention is not limited to the mechanical, electro-optical system by which an object area is scanned, so long as the system provides data relating to the amplitude of the return. Further, the invention is not limited to the size, shape, or energy distribution of the spots used. For example, while the invention was described above with reference to a spot having a uniform energy distribution, one having the Gaussian energy shown in FIG. 4 could have been used as well. The curve 90 is shown as being linear on a Gaussian graph with the abscissa being the percent of beam energy or R and the ordinate being the displacement from center or edge location as a fraction of $1/e$ radius.

It is intended by the appended claims to cover any and all such modifications, applications, and embodiments within the scope of the invention.

Accordingly,

What is claimed is:

1. An improved inspection system comprising:
   means for scanning with a beam of electromagnetic energy, an object area having first and second contiguous sections of first and second degrees of reflectivity or transmissivity with respect to said beam;
   detecting means disposed to receive energy reflected from or transmitted through said object area for providing a first signal having a first measured value S representing the amplitude of energy instantaneously reflected from or transmitted through said object area; and
   processing means for analyzing said first signal and computing the ratio F of one of said first or second sections as a fraction of the total area instantaneously illuminated by said beam.

2. The improved inspection system of claim 1 wherein said processing means includes first storage means for providing a second value $A_S$ representing the amplitude of said first signal when said beam illuminates an area having said first section exclusively.

3. The improved inspection system of claim 2 wherein said processing means includes second storage means for providing a third value $A_M$ representing the amplitude of said first signal when said beam illuminates an area having said second section exclusively.

4. The improved inspection system of claim 3 wherein said processing means includes means for subtracting from the amplitude S of said first signal, said second value $A_S$ to provide a first difference.

5. The improved inspection system of claim 4 wherein said processing means includes means for subtracting said second value $A_S$ from said third value $A_M$ to provide a second difference.

6. The improved inspection system of claim 5 wherein said processing means includes means for dividing said first difference by said second difference to compute the ratio F of one of said first or second sections as a fraction of the total area instantaneously illuminated by said beam.

7. In an inspection system having means for scanning with a beam of electromagnetic energy, an object area having first and second contiguous sections of first and second degrees of reflectivity or transmissivity with respect to said beam; and detecting means disposed to receive energy reflected from or transmitted through said object area; an improvement comprising:
   means connected to said detecting means for providing a first signal having a first measured value S representing the amplitude of energy instantaneously reflected from or transmitted through said object area; and
   processing means for analyzing said first signal and computing the ratio F of one of said first or second sections as a fraction of the total area instantaneously illuminated by said beam, said processing means including
   first storage means for providing a second value $A_S$ representing the amplitude of said first signal when said beam illuminates an area having said first section exclusively,
   second storage means for providing a third value $A_M$ representing the amplitude of said first signal when said beam illuminates an area having said second section exclusively,
   means for subtracting from the amplitude S of said first signal, said second value $A_S$ to provide a first difference,
   means for subtracting said second value $A_S$ from said third value $A_M$ to provide a second difference, and
   means for dividing said first difference by said second difference to compute the ratio F of one of said first or second sections as a fraction of the total area instantaneously illuminated by said beam.

8. In an optical system having means for scanning with a beam of electromagnetic energy, an object area having first and second contiguous sections of first and second degrees of reflectivity or transmissivity with respect to said beam; and detecting means disposed to receive energy reflected from or transmitted through said object area and to provide a first signal; a technique including the steps of:
   (a) measuring the amplitude of said first signal to provide a first measured value S representing the amplitude of energy instantaneously reflected from or transmitted through said object area; and (b) analyzing said first signal and computing the ratio F of one of said first or second sections as a fraction of the total area instantaneously illuminated by said beam.

9. The technique of claim 8 wherein said step of analyzing said first signal and computing the ratio F of one of said first or second sections as a fraction of the total area instantaneously illuminated by said beam includes the step of:

(c) storing a second value $A_S$ representing the amplitude of said first signal when said beam illuminates an area having said first section exclusively.

10. The technique of claim 9 wherein said step of analyzing said first signal and computing the ratio F of one of said first or second sections as a fraction of the total area instantaneously illuminated by said beam includes the step of:

(d) storing a third value $A_M$ representing the amplitude of said first signal when said beam illuminates an area having said second section exclusively.

11. The technique of claim 10 wherein said step of analyzing said first signal and computing the ratio F of one of said first or second sections as a fraction of the total area instantaneously illuminated by said beam includes the step of:

(e) subtracting from the amplitude S of said first signal, said second value $A_S$ to provide a first difference.

12. The technique of claim 11 wherein said step of analyzing said first signal and computing the ratio F of one of said first or second sections as a fraction of the total area instantaneously illuminated by said beam further includes the step of:

(f) subtracting said second value $A_S$ from said third value $A_M$ to provide a second difference.

13. The technique of claim 12 wherein said step of analyzing said first signal and computing the ratio F of one of said first or second sections as a fraction of the total area instantaneously illuminated by said beam further includes the step of:

(g) dividing said first difference by said second difference to compute the ratio F of one of said first or second sections as a fraction of the total area instantaneously illuminated by said beam.

* * * * *